US00PP34602P2

(12) United States Plant Patent
Smit

(10) Patent No.: US PP34,602 P2
(45) Date of Patent: Sep. 20, 2022

(54) ***KALANCHOE* PLANT NAMED 'EC-KALA-2109'**

(50) Latin Name: *Kalanchoe laciniata*
Varietal Denomination: EC-KALA-2109

(71) Applicant: Eden Collection, BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 17/677,708

(22) Filed: Feb. 22, 2022

(51) Int. Cl.
*A01H 5/02* (2018.01)
*A01H 6/32* (2018.01)

(52) U.S. Cl.
USPC ..... Plt./335
CPC ..... *A01H 6/324* (2018.05)

(58) Field of Classification Search
USPC ..... Plt./335
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Kalanchoe* plant named 'EC-KALA-2109' is disclosed, characterized by green leaves with serrated, white leaf margins, which vary in width. Plants have an upright, globular habit, with succulent, rounded branches. Flowering has not been observed. *Kalanchoe* is a popular genus, typically produced for the floriculture industry, as well as for uses as container plants for the patio, or as landscape plants. The new variety is suitable for both indoor and outdoor ornamental uses.

2 Drawing Sheets

Figure 1:
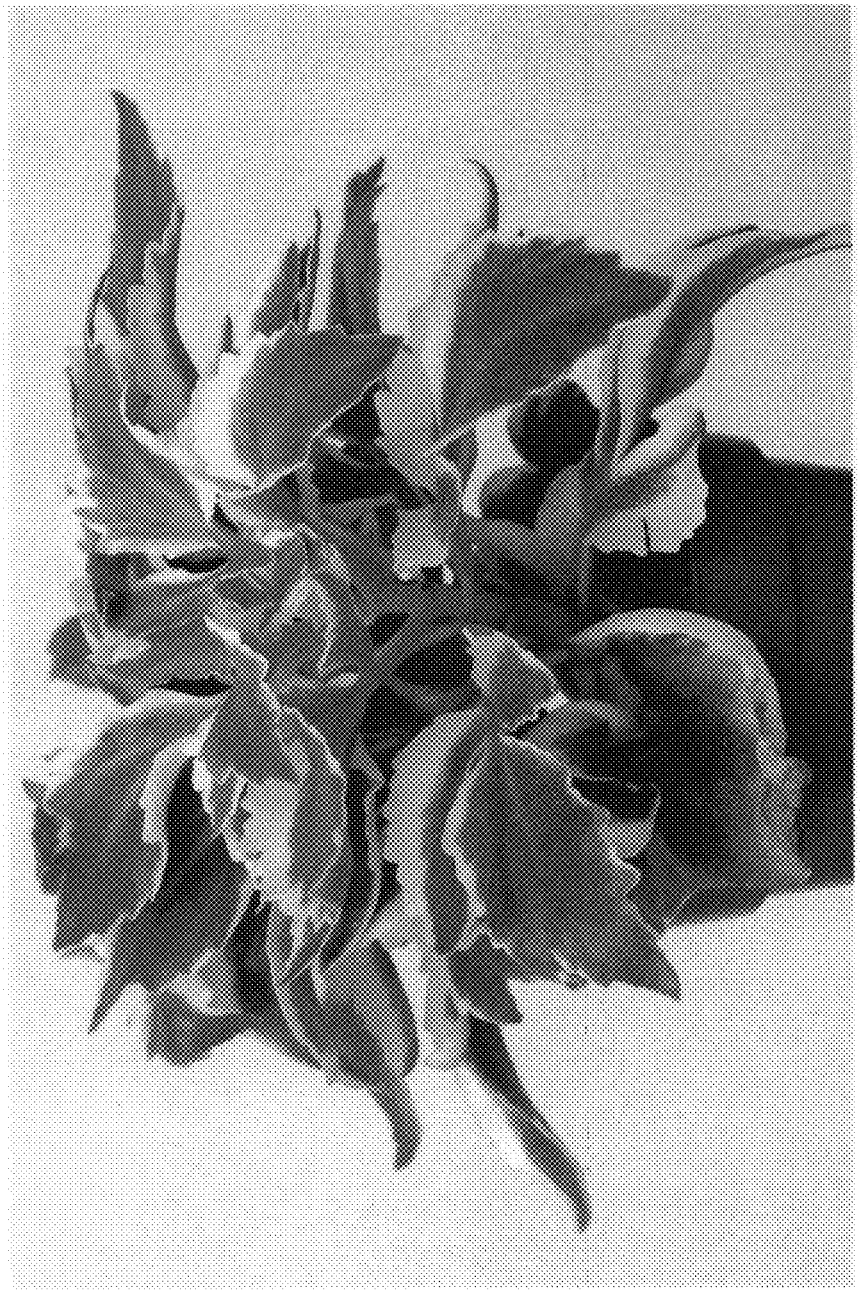

Latin name of the genus and species: *Kalanchoe laciniata.*

Variety denomination: 'EC-KALA-2109'.

BACKGROUND OF THE INVENTION

The new cultivar is a product of a naturally occurring branch mutation of an unnamed, unpatented *Kalanchoe laciniata* plant. The new variety was discovered by the inventor in 2019 at a nursery in Sappemeer, the Netherlands.

Asexual reproduction of the new cultivar 'EC-KALA-2109' was first performed at the same nursery in Sappemeer, the Netherlands, by vegetative terminal cuttings in April 2020. *Kalanchoe* 'EC-KALA-2109' has since produced multiple generations and has shown that the unique features of this cultivar are stable and reproduced true to type.

SUMMARY OF THE INVENTION

The cultivar 'EC-KALA-2109' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-KALA-2109'. These characteristics in combination distinguish 'EC-KALA-2109' as a new and distinct *Kalanchoe* cultivar:

1. Green leaves with a white leaf margin, which varies in width.
2. Serrated leaf margin.

PARENT COMPARISON

The new cultivar 'EC-KALA-2109' can be compared to the parent *Kalanchoe laciniata*. Plants of the *Kalanchoe laciniata* are similar to plants of the new cultivar 'EC-KALA-2109' in most horticultural characteristics. However, the new cultivar 'EC-KALA-2109' differs in the following:

1. Leaves of 'EC-KALA-2109' are green with a white leaf margin, while leaves of the parent *Kalanchoe laciniata* are fully green, without variegation.

COMMERCIAL COMPARISON

The new cultivar 'EC-KALA-2109' can be compared to an unnamed, unpatented *Kalanchoe beharensis* known to the inventor. Plants of this *Kalanchoe beharensis* are similar to plants of the new cultivar 'EC-KALA-2109' in most horticultural characteristics. However, the new cultivar 'EC-KALA-2109' differs in the following:

1. Leaves of 'EC-KALA-2109' are green with a white leaf margin, while leaves of this comparator are silver-grey.
2. Leaves of 'EC-KALA-2109' have a smooth surface, while those of this comparator are hairy.
3. Leaves of 'EC-KALA-2109' are smaller than those of this comparator.

The new cultivar 'EC-KALA-2109' can be compared to the unpatented commercial variety *Kalanchoe blossfeldiana* 'Debora', unpatented. Plants of *Kalanchoe* 'Debora' are similar to plants of the new cultivar 'EC-KALA-2109' in most horticultural characteristics. However, the new cultivar 'EC-KALA-2109' differs in the following:

1. Leaves of 'EC-KALA-2109' are green with a white leaf margin which varies in width, while leaves of *Kalanchoe* 'Debora' are green with a tiny white leaf margin.
2. Leaves of 'EC-KALA-2109' are bigger than those of *Kalanchoe* 'Debora'.
3. 'EC-KALA-2109' is more upright growing, while 'Debora' is more compact, rosette-like growing.

BRIEF DESCRIPTION OF THE PHOTOGRAPHS

The accompanying photograph in FIG. 1 illustrates in full color a typical plant of 'EC-KALA-2109' grown in a greenhouse. The plant is approximately 25 weeks of age.

Figure 2:
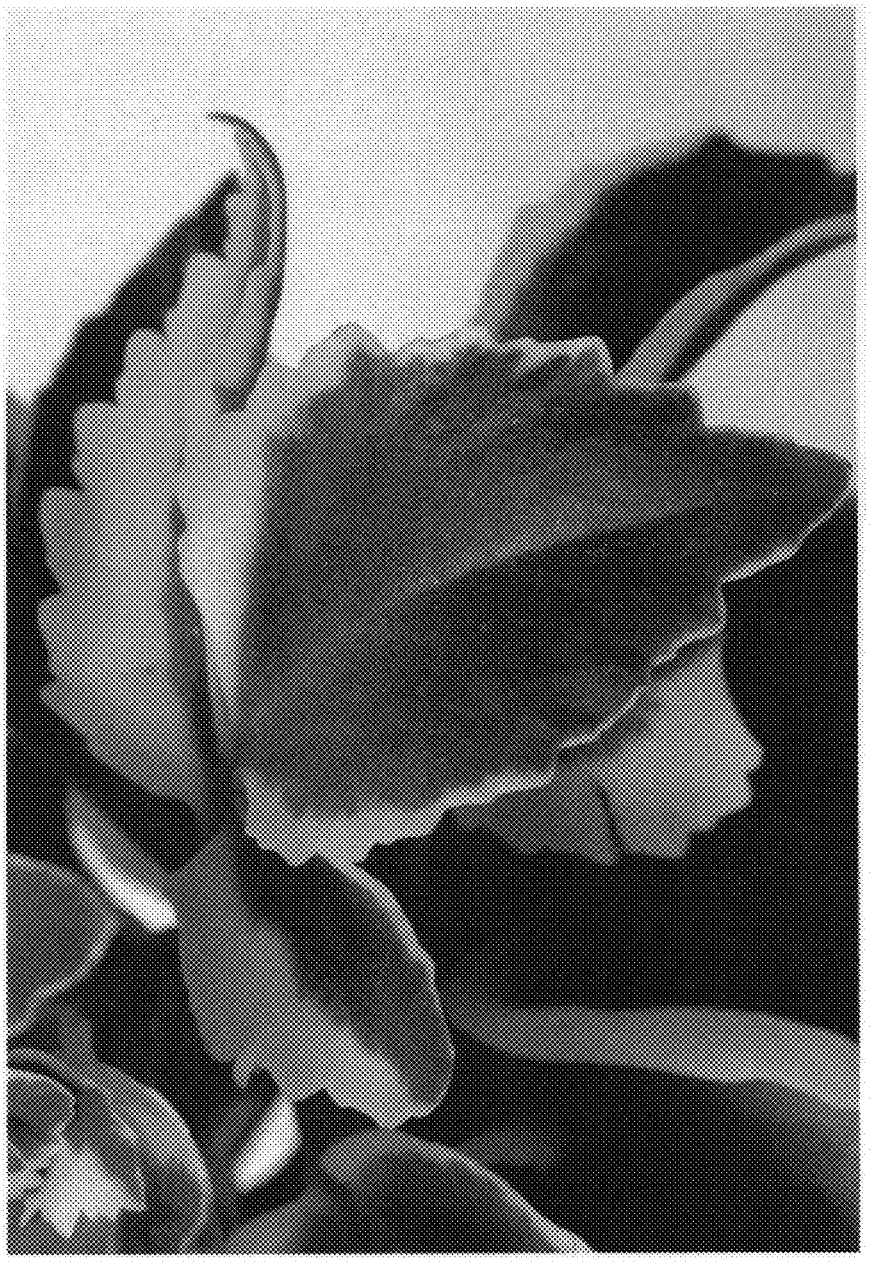

FIG. 2 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2015 except where general terms of ordinary dictionary significance are used. The following observations and measurements describe 'EC-KALA-2109' plants in a glass-greenhouse in Sappemeer, the Netherlands, in October. Temperatures ranged from 20° C. to 22° C. during the day, and 18° C. to 20° C. at night. No artificial light, photoperiodic treatments or chemical treatments were given to the plants. Natural light conditions were approximately 3000 to 3500 fc of light. Measurements and numerical values represent averages of typical plant types.

Botanical classification: *Kalanchoe laciniata* 'EC-KALA-2109'.

PROPAGATION

Type of propagation typically used: Top cuttings.

Time to initiate roots: About 10 days in summer; 12 days in winter, at approximately 21° C.

Root description: Fairly dense, fine, herbaceous, freely branching. Brown in color, not accurately measured with R.H.S. color chart.

PLANT

Age of plant described: Approximately 5 months from a cutting.

Container size of the plant described: 12 cm circular container; 5 top-cuttings per container.

Plant type: Perennial potted plant.

Shape: Globular.

Growth habit: Upright tender succulent.

Height: Approximately 16.4 cm from soil level to top of foliar plane.

Plant spread: Approximately 23.6 cm.

Growth rate: Moderate.

Plant vigor: Moderate.

Branching characteristics:

Length of primary lateral branches: About 10.9 cm.

Diameter of lateral branches: About 0.8 cm.

Quantity of primary lateral branches: Average 2.

Characteristics of primary lateral branches:

*Form*.—Succulent, thick, rounded.

*Texture*.—Glabrous.

*Color*.—Developing: RHS Yellow-Green 144B, covered with very thin waxy layer, lighter than 147D. Mature: RHS Yellow-Green 146D. At Internodes: Blend of RHS Yellow-Green 146D and 147D.

*Luster*.—Very slightly glossy.

*Aspect*.—Average 30°.

*Strength*.—Moderately strong.

Internode length: About 1.5 cm.

FOLIAGE

Leaf:

*Arrangement*.—Opposite, compound.

*Leaflets per leaf*.—Average 3.

*Leaves per main branch*.—Average 16 (8 pairs).

*Whole leaf length*.—10 cm.

*Whole leaf width*.—9.4 cm.

*Whole leaf shape*.—Broad ovate to near orbicular.

*Whole leaf aspect*.—Slightly concave to carinate.

*Leaflet apex*.—Acute.

*Leaflet base*.—Central (top) leaflet attenuate; lateral leaflets narrow cuneate.

*Leaflet margin*.—Bluntly serrate-dentate to biserrate-dentate.

*Leaflet texture*.—Glabrous, smooth, leathery both surfaces.

*Leaflet pubescence*.—None.

*Leaflet rugosity*.—Non-rugose — both surfaces.

*Leaflet luster*.—Slightly glossy.

*Leaflet shape*.—Overall ovate to rounded deltate.

*Leaflet length*.—Average range 3 cm to 7 cm.

*Leaflet width*.—Average range 2.5 cm to 4.5 cm.

*Color*.—Young foliage, upper side: RHS Yellow-Green 143B, fading to Green 138B towards margins. Leaflet irregularly margined with a blend of Green-White 155A and 157C. Young foliage, under side: RHS Green to Greyed-Green, a blend of 138C and 191B; irregularly margined Yellow-Green to White, a blend of 150D and 155A. Mature foliage, upper side: RHS Green NN137A, fading to Greyed-Green 191A towards the margins; leaflet irregularly margined White 155A. Mature foliage, under side: RHS Greyed-Green 191A, fading to 191B towards margins; leaflet irregularly margined Yellow-Green to White, a blend of 150D and 155A.

*Venation*.—Pinnate.

*Venation color, upper side*.—RHS Yellow-Green 147B.

*Venation color, under side*.—RHS Yellow-Green 144A.

Petiole:

*Length*.—Average 2.6 cm.

*Diameter*.—Petiole flattened, average 0.7 cm at widest; 0.5 cm at narrowest.

*Texture*.—Glabrous, smooth.

*Luster*.—Upper Side: Matte. Under Side: Moderately glossy.

*Strength*.—Medium.

*Color*.—Upper Side: RHS Greyed-Green 194D; main vein 191B. Under Side: RHS Green 138B.

Petiolule:

*Length*.—Average range 8 mm to 11 mm.

*Diameter*.—3 mm to 5 mm.

*Texture*.—Glabrous.

FLOWER

Flowers not observed to date.

OTHER CHARACTERISTICS

Fruits and seeds: Not observed to date.

Temperature tolerance: Tolerates temperature to at least 40° C. Hardy to USDA zones 10 to 12.

Disease/pest resistance: Similar resistance or susceptibility to normal diseases and pests of other *Kalanchoe* varieties.

Drought tolerance: Similar resistance or tolerance of other *Kalanchoe* varieties.

What is claimed is:

1. A new and distinct cultivar of *Kalanchoe* plant named 'EC-KALA-2109' as herein illustrated and described.

* * * * *